(12) United States Patent
Gaudreault

(10) Patent No.: US 9,434,910 B2
(45) Date of Patent: Sep. 6, 2016

(54) MOLD AND MILDEW STAIN REMOVING SOLUTION

(71) Applicant: Rosemary Gaudreault, Park Ridge, IL (US)

(72) Inventor: Rosemary Gaudreault, Park Ridge, IL (US)

(73) Assignee: Jelmar, LLC, Skokie, IL (US)

( * ) Notice: Subject to any disclaimer, the term of this patent is extended or adjusted under 35 U.S.C. 154(b) by 0 days.

(21) Appl. No.: 13/694,898

(22) Filed: Jan. 16, 2013

(65) Prior Publication Data

US 2014/0199416 A1 Jul. 17, 2014

(51) Int. Cl.

| | | |
|---|---|---|
| A61K 33/00 | (2006.01) |
| C11D 1/825 | (2006.01) |
| C11D 3/48 | (2006.01) |
| C11D 3/20 | (2006.01) |
| C11D 3/33 | (2006.01) |
| A61L 2/00 | (2006.01) |
| A61L 2/18 | (2006.01) |
| A61L 2/16 | (2006.01) |
| C11D 1/72 | (2006.01) |
| C11D 1/75 | (2006.01) |

(52) U.S. Cl.
CPC .............. *C11D 1/825* (2013.01); *C11D 3/2068* (2013.01); *C11D 3/2086* (2013.01); *C11D 3/33* (2013.01); *C11D 3/48* (2013.01); *A61L 2/0082* (2013.01); *A61L 2/0088* (2013.01); *A61L 2/16* (2013.01); *A61L 2/18* (2013.01); *C11D 1/72* (2013.01); *C11D 1/75* (2013.01)

(58) Field of Classification Search
CPC .............. C11D 3/43; C11D 1/72; C11D 1/75
See application file for complete search history.

(56) References Cited

U.S. PATENT DOCUMENTS

| | | |
|---|---|---|
| 3,993,575 A | 11/1976 | Howanitz et al. |
| 4,294,764 A | 10/1981 | Rinehart |
| 4,690,779 A | 9/1987 | Baker et al. |
| 4,983,317 A | 1/1991 | Requejo et al. |
| 5,122,568 A | 6/1992 | de Pierne et al. |
| 5,139,614 A | 8/1992 | de Pierne et al. |
| 5,362,422 A | 11/1994 | Masters |
| 5,384,063 A | 1/1995 | Woo et al. |
| 5,399,280 A | 3/1995 | Woo et al. |
| 5,468,303 A | 11/1995 | Thomas, Sr. |
| 5,522,942 A | 6/1996 | Graubart et al. |
| 5,635,462 A | 6/1997 | Fendler et al. |
| 5,679,629 A | 10/1997 | Kubota et al. |
| 5,691,291 A | 11/1997 | Wierenga et al. |
| 5,700,772 A | 12/1997 | Isobe et al. |
| 5,783,537 A | 7/1998 | Ahmed et al. |
| 5,785,962 A | 7/1998 | Hinz et al. |
| 5,817,615 A | 10/1998 | Garabedian, Jr. et al. |
| 5,837,664 A | 11/1998 | Black |
| 5,922,672 A | 7/1999 | Stringer et al. |
| 5,925,606 A | 7/1999 | Stamm |
| 5,929,007 A | 7/1999 | Feng |
| 5,962,388 A | 10/1999 | Sherry et al. |
| 5,990,064 A | 11/1999 | Wierenga et al. |
| 5,990,066 A | 11/1999 | Gordon et al. |
| 5,998,358 A | 12/1999 | Herdt et al. |
| 6,015,780 A | 1/2000 | Llosas Bigora et al. |
| 6,017,872 A | 1/2000 | Pedersen et al. |
| 6,034,181 A | 3/2000 | Bazaj et al. |
| 6,086,634 A | 7/2000 | Smith |
| 6,103,686 A | 8/2000 | Asakawa et al. |
| 6,121,219 A | 9/2000 | Herdt et al. |
| 6,156,129 A | 12/2000 | Hlivka et al. |
| 6,204,230 B1 | 3/2001 | Taylor et al. |
| 6,251,845 B1 | 6/2001 | Herbots et al. |
| 6,277,805 B1 | 8/2001 | Kupneski |
| 6,281,182 B1 | 8/2001 | Leonard et al. |
| 6,306,805 B1 | 10/2001 | Bratescu et al. |
| 6,346,508 B1 | 2/2002 | Leonard et al. |
| 6,384,010 B1 | 5/2002 | Wagers |
| 6,399,563 B1 | 6/2002 | Durbut et al. |
| 6,423,674 B1 | 7/2002 | Williams et al. |

(Continued)

FOREIGN PATENT DOCUMENTS

| | | |
|---|---|---|
| CA | 2276165 | 12/1999 |
| GB | 1240469 | 7/1971 |

(Continued)

OTHER PUBLICATIONS

International Search Report and Written Opinion of PCT Application No. US2013/41148, mailed Sep. 27, 2013, 9 pages.

(Continued)

*Primary Examiner* — James Rogers
(74) *Attorney, Agent, or Firm* — Greenberg Traurig, LLP

(57) ABSTRACT

A solution having improved mold and mildew stain removing properties on hard surfaces, that is easier to handle (less corrosive and less malodorous) and that is environmentally friendly. The mold and mildew stain removing solution includes the following components: a surfactant selected from the group consisting of alcohol ethoxylates, alkyl sulfates, alkyl ether sulfates, alpha olefin sulfonates, alkyl phosphates, alkyl amidopropyl betaines, alkyl betaines, amphoacetates, amphoproprionates, amphosulfonates, amine oxides, alkanolamides, sulfosuccinates, and sultaines, a solvent, and at least one chelating agent. The solution may further comprise a hydrotrope, a diluent, a preservative, and/or a fungicide. The surfactant is preferably an alcohol ethoxylate. The hydrotrope is preferably lauramine oxide. The solvent is preferably a glycol ether. The chelating agents are preferably sodium gluconate and a solution of the trisodium salt of methyl glycine diacetic acid.

11 Claims, No Drawings

(56) References Cited

U.S. PATENT DOCUMENTS

| | | |
|---|---|---|
| 6,423,677 B1 | 7/2002 | Van Eenam |
| 6,425,959 B1 | 7/2002 | Man |
| 6,429,182 B1 | 8/2002 | Julemont et al. |
| 6,429,183 B1 | 8/2002 | Leonard et al. |
| 6,432,395 B1 | 8/2002 | Rochon et al. |
| 6,436,445 B1 | 8/2002 | Hei et al. |
| 6,436,885 B2 | 8/2002 | Biedermann et al. |
| 6,436,892 B1 | 8/2002 | Leonard et al. |
| 6,451,748 B1 | 9/2002 | Taylor et al. |
| 6,479,453 B2 | 11/2002 | Man |
| 6,489,285 B2 | 12/2002 | Faber |
| 6,551,985 B1 | 4/2003 | Bianchetti et al. |
| 6,559,111 B2 | 5/2003 | Colurciello, Jr. et al. |
| 6,605,584 B2 | 8/2003 | Fong et al. |
| 6,617,303 B1 | 9/2003 | Smith et al. |
| 6,627,586 B1 | 9/2003 | Brooks et al. |
| 6,627,590 B1 | 9/2003 | Sherry et al. |
| 6,660,706 B1 | 12/2003 | Koester et al. |
| 6,699,825 B2 | 3/2004 | Rees et al. |
| 6,699,828 B1 | 3/2004 | de Buzzaccarini et al. |
| 6,740,626 B2 | 5/2004 | Neumiller |
| 6,794,346 B2 | 9/2004 | Wick |
| 6,821,939 B1 | 11/2004 | Szewczyk et al. |
| 6,933,267 B2 | 8/2005 | Colurciello et al. |
| 7,094,742 B2 | 8/2006 | Gaudreault |
| 7,144,846 B2 | 12/2006 | Keller et al. |
| 7,368,417 B2 | 5/2008 | Gaudreault |
| 7,517,842 B2 | 4/2009 | Barnhart et al. |
| 7,597,766 B2 | 10/2009 | Mcrae et al. |
| 7,622,606 B2 | 11/2009 | Smith et al. |
| 7,699,941 B2 | 4/2010 | Pivonka et al. |
| 7,745,384 B2 | 6/2010 | Perry et al. |
| 7,893,014 B2 | 2/2011 | Van Buskirk et al. |
| 7,951,766 B1 | 5/2011 | Frenkel et al. |
| 8,222,194 B2 | 7/2012 | Trivedi et al. |
| 2001/0023127 A1 | 9/2001 | Andreas |
| 2001/0034313 A1 | 10/2001 | Honda et al. |
| 2002/0187918 A1 | 12/2002 | Urban |
| 2003/0019508 A1 | 1/2003 | Tomarchio et al. |
| 2003/0099570 A1 | 5/2003 | Barnabas et al. |
| 2003/0100465 A1 | 5/2003 | Kilkenny et al. |
| 2003/0216281 A1 | 11/2003 | De Leo et al. |
| 2003/0224958 A1 | 12/2003 | Andreas |
| 2004/0023834 A1 | 2/2004 | Inoue et al. |
| 2005/0239676 A1 | 10/2005 | Gaudreault |
| 2005/0282722 A1 | 12/2005 | McReynolds et al. |
| 2006/0223735 A1 | 10/2006 | Gaudreault |
| 2008/0267900 A1 | 10/2008 | Steinbrenner et al. |
| 2009/0324964 A1 | 12/2009 | Jaynes et al. |
| 2010/0022644 A1 | 1/2010 | Smith et al. |
| 2010/0155659 A1 | 6/2010 | Yang et al. |
| 2010/0184855 A1* | 7/2010 | Bernhardt et al. ............ 514/529 |
| 2012/0122756 A1 | 5/2012 | Gaudreault |
| 2012/0122757 A1 | 5/2012 | Gaudreault |

FOREIGN PATENT DOCUMENTS

| | | |
|---|---|---|
| WO | 2008/042840 A1 | 4/2008 |
| WO | 2009/060171 A1 | 5/2009 |
| WO | 2009/137096 A1 | 11/2009 |
| WO | 2011049614 A2 | 4/2011 |
| WO | 2012038755 | 3/2012 |
| WO | 2012/071059 A | 5/2012 |

OTHER PUBLICATIONS

Canadian Intellectual Property Office, Office Action issued on Canadian patent application No. 2,816,064, dated Dec. 30, 2013, 6 pages.

Canadian Intellectual Property Office, Office Action issued on Canadian patent application No. 2,816,066, dated Dec. 30, 2013, 7 pages.

International Search Report and Written Opinion of PCT Application No. US2013/41160, mailed Oct. 1, 2013, 9 pages.

* cited by examiner

MOLD AND MILDEW STAIN REMOVING SOLUTION

BACKGROUND OF THE INVENTION

1. Field of the Invention

The present invention relates in general to an improved solution for removing mold and mildew stains from hard surfaces, that is also environmentally friendly.

2. Background Art

Mold and mildew stain removing solutions have been known and used to remove mold and mildew stains from a variety of hard surfaces found in the home, such as wooden and concrete floors, stainless steel, painted walls and ceilings, floor and bath tiles, as well as plastic, fiberglass, composite or laminated materials. Mold and mildew stains appear on many surfaces in the home, most frequently where water or humidity is present, such as in the bathroom, kitchen, or in basement areas. Standing water, water-damaged materials, or wet surfaces serve as a breeding ground for mold and mildew. Mold and mildew also grow in homes affected by floods and water leaks, which dampen household surfaces and provide areas for mold and mildew to grow. Typically, a small amount of a solution is sprayed onto a surface to remove the mold and mildew stain. After waiting a few minutes for the solution to penetrate the mold and mildew stain, it is then typically wiped away, using a cloth or paper towel.

Mold and mildew stain removing solutions traditionally contain a high amount of solvent, that itself would have a high vapor pressure. Such solutions have proven effective at penetrating large accumulations of mold and mildew, but are increasingly disfavored. First, high vapor pressure solvents can quickly flash off from the solution after they are applied, leaving the solution unable to penetrate a deep stain. To compensate for this, additional solvent is often required. Second, solvents with a high vapor pressure often emit an odor that is unpleasant for the user, which is amplified by its high concentration in the solution. Third, such solvents often emit high amounts of volatile organic compounds (VOCs) that are the subject of increasing regulation and public concern, which limits their use in household products. Fourth, many of the solvents that have traditionally been used in mold and mildew stain removing solutions are not biodegradable—a characteristic increasingly rejected by customers and regulatory bodies alike. One popular solvent used in traditional mold and mildew stain removing solutions is 2-butoxyethanol, also known as "EB". EB has been cited by the Agency for Toxic Substances and Disease Registry for causing irritation of the nose and eyes, headache and vomiting. EB has also been found in at least 20 of the 1,430 National Priorities List (Superfund or Cleanup) sites identified by the Environmental Protection Agency.

Also, mold and mildew stain removing solutions have traditionally contained a higher pH level, such as 11.0 and higher. While high pH solutions have been effective at removing mold and mildew stains, their high pH levels pose problems for the cleaner, as well as for the surface that is being cleaned. First of all, direct contact with a high pH solution can dry out or even burn the skin; protective gloves must be worn by the user. Furthermore, the high pH solutions can also corrode hard surfaces while removing the mold and mildew stain. Prolonged exposure to a high pH cleaning solution can often result in corrosion to more delicate household surfaces.

It has also become important for mold and mildew stain removing solutions to be formulated in such a way as to have less impact on the environment (to be "green"). One way in which this is encouraged is through a program of the United States Environmental Protection Agency, known as the Design for the Environment Program ("DfE"). DfE certifies "green" cleaning products through the Safer Product Labeling Program. Another is through state regulatory bodies, such as the California Air Resources Board ("CARB"). Either through regulation, or through certification, these bodies set out standards for achieving environmentally friendly cleaning products. Among the standards, are the desire for a solution that is not as corrosive as prior art solutions, one having a lower pH. Further, the solution must minimize the emissions of VOCs, as well as the percentage of solvent that it may contain. Finally, the solution must contain only biodegradable products.

Accordingly, it is desirable to provide an effective mold and mildew stain removing solution, which is less corrosive than existing solutions for safer handling by the user, and to reduce the corrosive effects on household surfaces.

It is further desirable to provide an effective mold and mildew stain removing solution, that contains only biodegradable products, which are not malodorous, and meet all applicable environmental standards and regulations.

It is yet further desirable to find a mold and mildew stain removing solution which may be applied to hard surfaces, with a specific combination of surfactants, hydrotropes, solvents, chelating agents, preservatives and fungicides—all of which act in a synergistic manner to improve their effectiveness in removing mold and mildew stains.

SUMMARY OF THE INVENTION

The present invention is directed to a mold and mildew stain removing solution, which comprises a surfactant selected from the group consisting of alcohol ethoxylates, alkyl sulfates, alkyl ether sulfates, alpha olefin sulfonates, alkyl phosphates, alkyl amidopropyl betaines, alkyl betaines, amphoacetates, amphoproprionates, amphosulfonates, amine oxides, alkanolamides, sulfosuccinates, and sultaines; a solvent selected from the group consisting of glycol ethers; and a chelating agent; that is easier to handle and environmentally friendly; towards effectively removing mold and mildew stains from hard surfaces.

In one preferred embodiment of the invention, the surfactant is a hydrotrope. In yet another preferred embodiment of the invention, the surfactant is selected from the group consisting of alcohol ethoxylates. The surfactant may comprise about 1% to about 8% of the mold and mildew stain removing solution.

In another preferred embodiment of the invention, the solution further comprises a hydrotrope. The hydrotrope may comprise about 1% to about 5% of the mold and mildew stain removing solution. The hydrotrope may be selected from the group consisting of amine oxides. In a preferred embodiment of the invention, the hydrotrope is lauramine oxide.

In yet another preferred embodiment of the invention, the solvent is a low vapor pressure solvent. In a preferred embodiment of the invention, the solvent is dipropylene glycol n-butyl ether. The solvent may comprise about 0.5% to about 5% of the mold and mildew stain removing solution.

In a further preferred embodiment of the invention, the chelating agent comprises about 0.35% to about 4.25% of the mold and mildew stain removing composition. The chelating agent may be selected from the group consisting of sodium gluconate, a salt of methyl glycine diacetic acid, tartaric acid, potassium sodium tartrate, potassium tartrate, trisodium citrates, monosodium citrates, tripotassium citrate, monopotassium citrate, sodium lactate, and malic acid. In another preferred embodiment of the invention, the chelating agent is selected from the group consisting of sodium gluconate and a salt of methyl glycine diacetic acid. In a preferred embodiment of the invention, the chelating agent is a first chelating agent, and the solution further comprises a second chelating agent, the total of which comprises about 0.35% to about 4.25% of the mold and mildew stain removing solution. In one preferred embodiment of the invention, the first and second chelating agents are selected from the group consisting of sodium gluconate, a salt of methyl glycine diacetic acid, tartaric acid, potassium sodium tartrate, potassium tartrate, trisodium citrates, monosodium citrates, tripotassium citrate, monopotassium citrate, sodium lactate, and malic acid. In another preferred embodiment of the invention, the first and second chelating agents are selected from the group consisting of sodium gluconate and a salt of methyl glycine diacetic acid.

In yet another preferred embodiment of the invention, the mold and mildew stain removing solution further comprises a diluent, in about 75% to about 97% of the solution.

In another embodiment of the invention, the mold and mildew stain removing solution further comprises at least one preservative, in about 0.25% to about 3% of the mold and mildew stain removing solution. The preservative may be selected from the group consisting of potassium bicarbonate, 2-methyl-4-isothiazolin-3-one, 1,2-benzisothiazolin-3-one, 2-n-octyl-4-isothiazolin-3-one, 2-methyl-4-isothiazolin-3-one, 5-chloro-2-methyl-4-isothiazolin-3-one, n-octyl-isothiazolin-3-one, DMDM hydantoin, iodopropynyl butylcarbamate, 2-bromo-2-nitropropan-1,3-diol, hexahydro-1,3,5-tris (2-hydroxyethyl)-s-triazine and poly (hexamethylenebiguanide) hydrochloride. In a preferred embodiment of the invention, the preservative is selected from the group consisting of potassium bicarbonate and 2-methyl-4-isothiazolin-3-one.

In yet another preferred embodiment of the invention, the mold and mildew stain removing solution further comprises at least one fungicide, in about 0.25% to about 3% of the mold and mildew stain removing solution. The fungicide may be selected from the group consisting of potassium bicarbonate, sodium bicarbonate, potassium carbonate, sodium carbonate, silver, cadmium, sulfur, tea tree oil, cinnamon essential oil, jojoba oil, neem oil, rosemary oil, monocerin, milk, and amepelomyces quisqualis AQ10.

In another preferred embodiment of the mold and mildew stain removing solution, the solution has a pH of about 9.2 to about 9.6.

DETAILED DESCRIPTION OF THE INVENTION

While this invention is susceptible of embodiment in many different forms, there are described herewithin several specific embodiments, with the understanding that the present disclosure is to be considered as an exemplification of the principals of the invention and is not intended to limit the invention to the embodiments so described.

The present invention is directed to a mold and mildew stain removing solution which is particularly suited for removing mold and mildew stains from various hard surfaces found in homes, such as wooden and concrete floors, stainless steel, painted walls and ceilings, floor and bath tiles, as well as plastic, fiberglass, composite or laminated materials. The present invention includes a solution that is effective at removing mold and mildew stains, while protecting the surface from the deleterious effects of corrosion, and safeguarding the environment.

The mold and mildew stain removing solution of the present invention comprises at least a surfactant selected from the group consisting of alcohol ethoxylates, alkyl sulfates, alkyl ether sulfates, alpha olefin sulfonates, alkyl phosphates, alkyl amidopropyl betaines, alkyl betaines, amphoacetates, amphoproprionates, amphosulfonates, amine oxides, alkanolamides, sulfosuccinates, and sultaines; a solvent; and a chelating agent. In a preferred embodiment of the invention, the mold and mildew stain removing solution also includes a hydrotrope compound. The solution may further comprise another chelating agent, a diluent, one or more preservatives and/or a fungicide.

The surfactant in the present mold and mildew stain removing solution performs the very important function of acting to physically separate a contaminating substance, from the surface to which the contaminating substance is adhered. The hydrotrope aides in the solubility of the surfactant, such that a higher amount of surfactant may be placed in solution to improve the performance of the mold and mildew stain removing solution. The chelating agents act to remove metal ions, which are required to sustain the underlying bacterial and fungal components of mold and mildew stain, and further assist in their adherence to the household surface. After the mold and mildew is separated by the surfactant and chelating agent, the solvent functions to dislodge the contaminant from the surface matrix, such that the mold and mildew stain may then adhere to a paper towel or cloth. The solvents may also dissolve dirt, oil, grease, and sebaceous material (such as natural oils and waxes present in skin that are emitted from the body in humid areas such as showers), which often adhere to the mold and mildew, and to the surface.

In a preferred embodiment of the invention, the mold and mildew stain removing solution includes a surfactant, a hydrotrope, a solvent, two chelating agents, a diluent, two preservatives and a fungicide.

Surfactant

As stated above, preferably the surfactant is selected from the group consisting of alcohol ethoxylates, alkyl sulfates, alkyl ether sulfates, alpha olefin sulfonates, alkyl phosphates, alkyl amidopropyl betaines, alkyl betaines, amphoacetates, amphoproprionates, amphosulfonates, amine oxides, alkanolamides, sulfosuccinates, and sultaines. The surfactant is preferably an alcohol ethoxylate. Alcohol Ethoxylates ("AEs") have the advantage that they are not affected by water hardness or pH changes, and in many cases it is an advantage that they are considered medium to low foaming agents. AEs are prepared commercially by the reaction of an alcohol and ethylene oxide. An example of the chemical structure of an alcohol ethoxylate is shown below:

$$CH_3(CH_2)_{x-y}O(CH_2CH_2O)_nH$$

x-y is the range of carbon units n is the average number of ethylene oxide units Structurally, AEs can be abbreviated as $C_{x-y}AE_n$ where the subscript following the 'C' indicates the range of carbon chain units. AEs with a carbon unit range between C3 to C16, are most commonly used in household detergent products. Further AEs contain an ethylene oxide (E) chain attached to the alcohol. The degree of ethylene oxide polymerization is indicated by the subscript 'n' which indicates the average number of ethylene oxide units, where units are ethylene oxide chains within the alcohol ethoxylate molecule. In household products, the ethylene oxide commonly ranges between 3 and 20 units. The fact that each product contains a mixture of molecules that covers a range of chain lengths (both in the alcohol and in the ethoxylate chain) has importance to the health and safety evaluation of AEs. The functional characteristics of two related products may be different, but their biological effects should be comparable.

The preferred AE surfactant of the present invention is Tomadol 900, comprising from about 1% to about 8% of the mold and mildew stain removing solution, most preferably in a 3.15% concentration in the formulation. Tomadol is a trademark owned by Tomah Products, Inc., of Milton, Wis. Tomadol 900 is commercially available from Air Products & Chemicals, Inc., of Allentown, Pa. Tomadol 900, CAS No. 68439-46-3, comprises 60-100% C9-11 AEs, including C9-11AE4, C9-11AE6, and $C_{9-11}AE8$. Other surfactant chemical groups that may be used in the present invention include: alkyl sulfates, alkyl ether sulfates, alpha olefin sulfonates, alkyl phosphates, alkyl amidopropyl betaines, alkyl betaines, amphoacetates, amphoprionates, amphosulfonates, amine oxides, alkanolamides, sulfosuccinates, and sultaines.

Hydrotrope

A hydrotrope acts to improve the solubility of surfactants in aqueous solutions. Couplers, like solvents and more-soluble surfactant classes, can also be used to increase solubility. Hydrotropes are a special class of couplers requiring relatively low levels for solubilization of surfactants. A higher concentration of hydrotrope generally leads to higher cloud points, the point at which the surfactant concentration is large enough such that some of the surfactant will solidify, and thus fall out of solution. Hydrotropes are known to be useful in formulations containing a surfactant.

A wide range of molecular structures can lead to hydrotropic behavior. Usual hydrotropes present a weak amphiphilic character, with small hydrophilic and hydrophobic moieties. They can be, among others, aromatic salts (sodium xylene sulfonate SXS), aromatic alcohols (pyrogallol) or short-chain soaps (sodium n-pentanoate). Medium and short-chain alkylpolyglucosides (APG) have also been regarded as hydrotropes, as have been more unusual compounds such as long chain dicarboxylic acids. Short-chain amphiphiles derived from ethylene glycol (CiEj), propylene glycol (CiPj) or glycerol (CiGly1) also present hydrotropic properties. These compounds are sometimes called "solvosurfactants" because they combine properties of surfactants (molecular structure surface-active properties) and of solvents (volatility, dissolving power).

Commercially available hydrotropes that may be used in association with the present invention include: b-alanine, n-(2-carboxyethyl)- and n-[3-(C12-15-alkyloxy) propyl] derivatives, alkenyl dicarboxcylic acid anhydride, alkyl polysaccharide, alkyl glucosides, alkyl polyglycol ether ammonium methyl chloride, amine oxides (including cocamidopropylamine oxide, lauramine oxide, myristamine oxide, and soyamidopropylamine oxide), benzyl alcohol ethylate, d-glucopyranose alkyl glycosides, disodium coco-amphodipropionate, sulfonic acid based hydrotropes (including sodium cumenesulfonic acid, xylenesulfonic acid, and toluenesulfonic acid), methyl-oxirane polymer, modified carboxcylic acid, modified carboxylate, organo phosphate amphoteric, modified phosphate ester, aromatic phosphate ester, natural fatty alcohol alkyl polyglucosides, potassium cocoate, sodium-n-lauryl-β-iminodipropionate, sodium octane sulfonate, and salts thereof.

There are several factors that must be considered in arriving at an appropriate hydrotrope. The hydrotrope must be compatible with the solvent, to ensure that the compounds are mutually soluble, and their surface tension must be low to allow the surfactant to penetrate the stain. Other considerations include cost, and synergistic effects when used in combination with a particular surfactant. It should be noted that there are some surfactants that also have the properties of a hydrotrope, and many of the hydrotropes listed above are also surfactants. Thus, a single chemical can be used as both the surfactant and the hydrotrope of the present invention. Such an arrangement often raises significant cost considerations.

The preferred hydrotrope to be used in the current invention is an amine oxide; more preferably, lauramine oxide ("LO"), which is also known as lauryldimethylamine oxide, dodecyldimethylamine oxide, or dimethyldodecylamine-N-oxide, comprising from about 1% to about 5% of the mold and mildew stain removing solution, most preferably 2.2% active in the formula. Lauramine oxide can be purchased under the trade name Mackamine LO from Rhodia Inc., located in Cranbury, N.J. Mackamine is a trademark owned by the McIntyre Group, Ltd., of University Park, Ill. Other alternative sources of lauramine oxide are Macat AO-12 (from Mason Chemicals) and Ammonyx LO (from Stepan Chemical). The addition of lauramine oxide as the hydrotrope has been found to increase the solubility of the surfactant, as intended, and also to increase the stability of the solution at higher temperatures. The solution described herein, with Tomadol as the surfactant and lauramine oxide as the hydrotrope, was found to be stable at temperatures as high as 50° C. for three months.

In addition to its properties as a hydrotrope, and as an example of the present invention, lauramine oxide has been found to generate an unexpected, synergistic effect—when used in combination with Tomadol as a surfactant, and the other ingredients of the mold and mildew stain removing solution described herein, such as a solvent and chelating agent. The addition of lauramine oxide as a hydrotrope was found to increase the mold and mildew stain removing performance to levels that were only known to be possible with more corrosive solutions that have a higher pH level.

Solvent

Suitable solvents that may be used with the present invention include glycol ethers. Of those solvents, the ones preferable for use in association with the present invention are low vapor pressure ("LVP") solvents, which also have a high flash point. LVP solvents are desirable for their solvent properties, while limiting VOC emissions in the resulting mold and mildew stain removing solutions. While high vapor pressure solvents may be desirable because of their performance, their use in a mold and mildew stain removing solution may create a higher than desirable level of VOC emissions. A high flash point refers to the temperature at which the solvent may ignite. Highly flammable solvents, such as acetone, ignite at lower temperatures, and therefore have a low flash point. Products that have a low flash point are not desirable for use or storage in the home. Other criteria that should be evaluated in choosing an appropriate solvent include solubility, stability in product, surface tension and cleaning ability.

The preferred glycol ether solvent is dipropylene glycol n-butyl ether, sold under the trade name Dowanol DPnB, comprising from about 0.5% to about 5% of the mold and mildew stain removing solution, most preferably 2% active in the formula. It is believed that the Dowanol DPnB solvent is especially helpful in two different, material aspects. First, it appears to help lower the surface tension, improving the efficiencies of the surfactant and chelating agents in solution. Second, this solvent appears to dissolve dirt, oil, grease and sebaceous material that can attach to the mold and mildew, and to the surface. Dissolving such materials is believed to assist in removing mold and mildew stains, by removing material that enables it to cling to a surface. Finally, these two advantages are believed to assist each other, in that dissolving dirt, oil, grease and sebaceous material further allows penetration of additional surfactant into the mold and mildew matrix.

Other Dowanol low vapor pressure solvents that may be used with the present invention include Dowanol TMP, Dowanol DPnP, Dowanol TPnB, Dowanol PPh, Dowanol EPh, and Dowanol DPMA. Other low vapor pressure glycol ethers that may be used include Carbitol, butyl Carbitol, Hexyl Carbitol, and butyl Carbitol acetate. Both Dowanol and Carbitol are trademarks owned by The Dow Chemical Company, of Midland, Mich.

Chelating Agents

One or more chelating agents are used in the present invention to remove metal ions from the surface containing mold or mildew. The bacteria and fungi in mold and mildew require certain metal ions, including magnesium, calcium and iron. The chelating agent acts to remove the metal ions from the bacteria and fungi. Without access to the metal ions, the bacteria and fungi cannot thrive, and are then more easily removed from the surface.

Preferably, two chelating agents are used in the present invention. The first preferred is sodium gluconate, preferably comprising from about 0.25% to about 3% of the mold and mildew stain removing solution, most preferably 1.75% active in the formula. Sodium gluconate is available from PMP Fermentation, of Peoria, Ill. The second preferred chelating agent is Trilon M, a solution of the trisodium salt of methyl glycine diacetic acid, comprising from about 0.1% to about 1.25% of the mold and mildew stain removing solution, most preferably 0.75% active in the formula. Trilon is a trademark owned by BASF Corporation, of Ludwigshafen, Germany. Trilon M is commercially available in the United States from BASF Corporation, of Florham Park, N.J. Each of these products are non-toxic biodegradable.

The amount of sodium gluconate that may be added to the mold and mildew stain removing solution is limited because of its low solubility. Trilon M has been found to be effective in working with sodium gluconate to extend the chelating function. While Trilon M may be employed as the only chelating agent in the mold and mildew stain removing solution, such an approach creates higher cost implications. Unexpectedly, the use of Trilon M, in combination with the preferred glycol ether solvent, appears to yield high mold and mildew stain removal efficiencies, even at a lower pH level than traditional mold and mildew stain removing solutions.

Other chelating agents that may be used with the present invention include tartaric acid, potassium sodium tartrate, potassium tartrate, trisodium citrates, monosodium citrates, tripotassium citrate, monopotassium citrate, sodium lactate, and malic acid. Other criteria should be considered in selecting an appropriate chelating agent, including solubility, stability, effectiveness within the expected pH range, effectiveness with the other chelating agents being used, toxicity, and biodegradability.

Remaining Ingredients

Other components that may be added to the mold and mildew stain removing solution, include a diluent, a preservative, and/or a fungicide.

The diluent is preferably deionized water, added to achieve the desired concentrations of the active ingredients in the solution, as well as to reduce the vapor pressure. The diluent of the present invention comprises about 75% to about 97% of the mold and mildew stain removing solution, most preferably 82%. While the diluent is not an active component in removing mold and mildew stains, its addition to the mold and mildew stain removing solution is highly desirable, because the active ingredients are typically available in a highly concentrated form. Therefore, a diluent can reduce the concentrations of the active constituents to their desired amounts.

The addition of one or more preservatives, has been shown to increase the effectiveness of the present mold and mildew stain removing solution invention. A preservative works to prevent the growth of bacteria, yeast and mold in the mold and mildew stain removing solution, and on the surface after it is applied. Two preservatives are preferred for use in the present invention. The first preservative is potassium bicarbonate, comprising from about 0.25% to about 3% of the mold and mildew stain removing solution, most preferably 0.45% active in the formula as a preservative. The second preservative is Neolone M-10, a chemical having the formula 2-methyl-4-isothiazolin-3-one, comprising from about 0.001% to about 0.015% of the mold and mildew stain removing solution, most preferably 0.014% active in the formula. Neolone is a trademark of The Rohm & Haas Company, of Philadelphia, Pa. Two different preservatives are used, because each is directed towards different organisms, their selection was found to be cost-effective—and most importantly, the use of both yielded successful results. Neolone M-10 is known to be effective against bacteria, but not against yeast or mold. Potassium bicarbonate is known to be effective against yeast and mold, and is also used as the fungicide, as discussed below. Additional criteria that should be evaluated in selecting appropriate preservatives include their ability to work in conjunction with the chelating agents, solubility, stability, effectiveness within the expected pH range, toxicity, and biodegradability. Other preservatives that may be used with the present invention include 1,2-benzisothiazolin-3-one, 2-n-octyl-4-isothiazolin-3-one, 2-methyl-4-isothiazolin-3-one, 5-chloro-2-methyl-4-isothiazolin-3-one, n-octyl-isothiazolin-3-one, DMDM hydantoin, iodopropynyl butylcarbamate, 2-bromo-2-nitropropan-1,3-diol, hexahydro-1,3,5-tris (2-hydroxyethyl)-s-triazine and poly (hexamethylenebiguanide) hydrochloride.

Finally, a fungicide may also be added to increase the effectiveness of the mold and mildew stain removing solution. A fungicide works to prevent the growth of fungi in the mold and mildew stain removing solution, and on the surface after it is applied. The preferred fungicide for use with the present invention is potassium bicarbonate, comprising from about 0.25% to about 3% of the mold and mildew stain removing solution, most preferably 0.95% active in the formula as a fungicide. It should be noted that in the preferred embodiment of the present invention, potassium bicarbonate is added as both a preservative and the fungicide, for a total of 1.4% active in the formula. The criteria that should also be considered in selecting an appropriate fungicide include their ability to work in conjunction with the chelating agents, solubility, stability, effectiveness within the expected pH range, toxicity, and biodegradability. Other fungicides that may be used with the present invention include sodium bicarbonate, potassium carbonate, sodium carbonate, silver, cadmium, and sulfur compounds. Certain natural fungicides may also be used with the present invention, including tea tree oil, cinnamon essential oil, jojoba oil, neem oil, rosemary oil, monocerin, milk, and amepelomyces quisqualis AQ10.

According to the preferred embodiment of the invention disclosed above, the resulting pH of the solution is expected to be about 9.2 to about 9.6. Within this range, the other ingredients of the mold and mildew stain removing solution as disclosed above, have proven to be effective at removing mold and mildew stains, while not being too corrosive on the surfaces being treated, or for the user. If needed, a mild acid may be added to lower the pH to the desired level, to be determined by the operational ranges of the active ingredients. Suitable acids that may be added to the present invention include gluconic acid and lactic acid.

The following example is given to illustrate the mold and mildew stain removing solution of the present invention, but is not intended to limit the invention to the example included herewith. The following example specifically illustrates an exemplary and preferred formulation of the mold and mildew stain removing solution according to the present invention. It is to be understood that the examples are presented by means of illustration only and that further use of formulations that fall within the scope of the present invention and the claims herewith may be readily produced by one skilled in the art with the present disclosure before them.

Preparation Of The Solution Formulation

An example formulation illustrating an embodiment of the inventive mold and mildew stain removing solution of the present invention is described in detail in Table 1 below and was formulated generally in accordance with the following protocol.

EXAMPLE 1

Mold and Mildew Stain Removing Solution Formulation 1

A mold and mildew stain removing solution according to the first embodiment of the present invention was prepared, by introducing appropriate amounts of the indicated constituents, so as to attain the desired relative weight percentages indicated in Table 1 hereinafter, by first charging deionized water into a tank equipped with a mixer. Tomadol 900 was then added to the tank from below the surface of the liquid in the tank to minimize foaming, and mixed until the solution was clear. Lauramine oxide, in the form of Mackamine LO, was then added in the same manner, and mixed about 30 minutes until the solution was homogenous and clear. The solvent, Dowanol DPnB, was added after the Mackamine LO and Tomadol 900, and then mixed about 15 minutes until the solution was homogenous. One of the chelating agents, sodium gluconate, was then added, and mixed for 30 minutes until it was dissolved. The second chelating agent, Trilon M, was then added, and mixed for 15 minutes. The preservative Neolone M-10 was then added, and mixed in with the solution for fifteen minutes. Finally, the preservative/fungicide potassium bicarbonate was added, and mixed for 30 minutes, until the solution was clear.

Inasmuch as various ones of the raw material components of the mold and mildew stain removing solution are purchased in a form that is at least partially diluted with water, Table 1 provides the percentage of each component which is active in the raw material, the percentage of each particular component (active material and any water in the raw material solution) in the formula and the percentage of each component in the active portion of the formula.

TABLE 1

Mold & Mildew Stain Removing Solution Formulation 1

| Ingredient Name | % Active in Raw Material | % in Formula | % Active in Formula |
|---|---|---|---|
| Deionized Water | | 82.342 | N/A |
| Tomadol 900 (Air Products) | 100 | 3.150 | 3.150 |
| Mackamine LO (Rhodia) | 30 | 7.333 | 2.200 |
| Dowanol DPnB (Dow) | 100 | 2.000 | 2.000 |
| Sodium Gluconate (PMP Fermentation) | 100 | 1.750 | 1.750 |
| Trilon M solution (BASF) | 40 | 1.875 | 0.750 |
| Neolone M-10 solution (Rohm & Haas) | 9.5 | 0.150 | 0.014 |
| Potassium Bicarbonate (Armand Products) | 100 | 1.400 | 1.400 |

Testing of Example Solution Formulation

The mold and mildew stain removing solution of the present invention was evaluated for mold and mildew stain removing performance, in comparison to two commercially available reference solutions that are currently marketed as mold or mildew stain removers. Mold & Mildew Stain Removing Solution Formulation 1 (Solution Formulation 1) was subjected to testing by an independent laboratory to measure the formulation's ability to remove mold and mildew stains that were grown on various surfaces, as detailed in Table 2. The test sample incubation, aging and fungal culture inoculation and growth were performed according the ASTM D3273 and ASTM G21 methods. The sample scoring was performed based on the scoring of fungal defacement provided in ASTM D3273.

TABLE 2

Comparison Testing of Mold & Mildew Stain Removing Solution Formulation 1

| Substrate | Solution Formulation 1 | Reference Solution A | Reference Solution B |
|---|---|---|---|
| Plastic | 10.67 | 8.89 | 6.00 |
| Stainless Steel | 12.21 | 13.43 | 9.33 |
| Ceramic | 8.00 | 5.33 | 8.54 |
| Fiberglass | 6.66 | 3.00 | 2.66 |
| 4-Square Tile/Grout | 8.66 | 9.33 | 7.77 |
| Wood | 8.00 | 8.54 | 6.66 |

As shown above, the Mold & Mildew Stain Removing Solution Formulation 1 was effective in removing mold and mildew stains from the substrates, often at levels either equivalent to, or even far surpassing, the removals measured for the commercially available reference solutions. In particular, the mold and mildew stain removing solution unexpectedly proved to be much more effective in removing mold and mildew stains from plastic and fiberglass surfaces, in comparison to the reference solutions, and better performing on tile and wood surfaces than certain of the reference solutions. In addition, Mold & Mildew Stain Removing Solution Formulation 1 has significant other benefits over the reference solutions, in that it is less likely to corrode the surfaces that are treated, and have lower odor associated with its use. Furthermore, the reference solutions are not believed to meet all of the same environmental standards, and thus may not be available if consumers or regulatory bodies further limit such VOC-emitting products.

While this invention is susceptible of embodiment in many different forms, there is shown in the drawings and will herein be described in detail, several preferred embodiments, with the understanding that the present disclosure should be considered as an exemplification of the principles of the invention and is not intended to limit the invention to the embodiment so illustrated.

The invention claimed is:

1. A mold and mildew stain removing solution comprising:
 a surfactant selected from the group consisting of alcohol ethoxylates, alkyl sulfates, alkyl ether sulfates, alpha olefin sulfonates, alkyl phosphates, alkyl amidopropyl betaines, alkyl betaines, amphoacetates, amphopropionates, amine oxides, alkanolamides, sulfosuccinates, and sultaines, wherein the surfactant comprises about 1 wt. % to about 8 wt. % of the solution;
 an amine oxide hydrotrope, wherein the hydrotrope comprises about 1 wt. % to about 5 wt. % of the solution;
 a glycol ether solvent, wherein the solvent comprises about 0.5 wt. % to about 5 wt. % of the solution;
 a first chelating agent, wherein the first chelating agent is sodium gluconate comprising about 0.25 wt. % to about 3 wt. % of the solution; and
 a second chelating agent, wherein the second chelating agent is a salt of methyl glycine diacetic acid comprising about 0.1 wt. % to about 1.25 wt. % of the solution,
 wherein the pH of the mold and mildew removing solution ranges from about 9.2 to about 9.6.

2. The mold and mildew stain removing solution of claim 1, wherein the surfactant is a hydrotrope.

3. The mold and mildew stain removing solution of claim 1, wherein the surfactant is an alcohol ethoxylate.

4. The mold and mildew stain removing solution of claim 1, wherein the amine oxide hydrotrope is lauramine oxide.

5. The mold and mildew stain removing solution of claim 1, wherein the solvent is dipropylene glycol n-butyl ether.

6. The mold and mildew stain removing solution of claim 1 wherein the solution further comprises a diluent, ranging from about 75 wt. % to about 97 wt. % of the mold and mildew stain removing solution.

7. The mold and mildew stain removing solution of claim 1 wherein the solution further comprises at least one preservative, ranging from about 0.25 wt. % to about 3 wt. % of the mold and mildew stain removing solution.

8. The mold and mildew stain removing solution of claim 7 wherein the preservative is selected from the group consisting of potassium bicarbonate, 2-methyl-4-isothiazolin-3-one, 1,2-benzisothiazolin-3-one, 2-n-octyl-4-isothiazolin-3-one, 2-methyl-4-isothiazolin-3-one, 5-chloro-2-methyl-4-isothiazolin-3-one, n-octyl-isothiazolin-3-one, DMDM hydantoin, iodopropynyl butylcarbamate, 2-bromo-2-nitropropan-1,3-diol, hexahydro-1,3,5-tris (2-hydroxyethyl)-s-triazine and poly (hexamethylenebiguanide) hydrochloride.

9. The mold and mildew stain removing solution of claim 7 wherein the preservative is selected from the group consisting of potassium bicarbonate and 2-methyl-4-isothiazolin-3-one.

10. The mold and mildew stain removing solution of claim 1 wherein the solution further comprises a fungicide, ranging from about 0.25 wt. % to about 3 wt. % of the mold and mildew stain removing solution.

11. The mold and mildew stain removing solution of claim 10 wherein the fungicide is selected from the group consisting of potassium bicarbonate, sodium bicarbonate, potassium carbonate, sodium carbonate, silver, cadmium, sulfur, tea tree oil, cinnamon essential oil, jojoba oil, neem oil, rosemary oil, monocerin, milk, and amepelomyces quisqualis AQ10.

* * * * *